(12) United States Patent
Konawa

(10) Patent No.: US 7,922,706 B2
(45) Date of Patent: Apr. 12, 2011

(54) ABSORPTIVE ARTICLE

(75) Inventor: Satoko Konawa, Sakura (JP)

(73) Assignee: Daio Paper Corporation, Ehime (JP)

( * ) Notice: Subject to any disclaimer, the term of this patent is extended or adjusted under 35 U.S.C. 154(b) by 266 days.

(21) Appl. No.: 11/922,178

(22) PCT Filed: Jun. 13, 2006

(86) PCT No.: PCT/JP2006/311816
§ 371 (c)(1),
(2), (4) Date: Dec. 13, 2007

(87) PCT Pub. No.: WO2006/134904
PCT Pub. Date: Dec. 21, 2006

(65) Prior Publication Data
US 2009/0326502 A1 Dec. 31, 2009

(30) Foreign Application Priority Data
Jun. 13, 2005 (JP) .................................. 2005-172319

(51) Int. Cl.
*A61F 13/15* (2006.01)
(52) U.S. Cl. ......... 604/385.28; 604/385.19; 604/385.24; 604/385.26; 604/385.27; 604/385.21
(58) Field of Classification Search ............. 604/385.19, 604/385.24, 385.26, 385.27, 385.28, 385.21, 604/385.101, 378
See application file for complete search history.

(56) References Cited

U.S. PATENT DOCUMENTS

| 5,718,698 A | * | 2/1998 | Dobrin et al. ................. 604/383 |
| 6,402,729 B1 | * | 6/2002 | Boberg et al. ............ 604/385.28 |
| 2003/0144644 A1 | | 7/2003 | Murai et al. |
| 2004/0249355 A1 | | 12/2004 | Tanio et al. |

FOREIGN PATENT DOCUMENTS

| JP | 8-229067 | 9/1996 |
| JP | 2002-000656 | 1/2002 |
| JP | 2003-210525 | 7/2003 |
| JP | 2003-245306 | 9/2003 |
| JP | 2004-358109 | 12/2004 |

* cited by examiner

*Primary Examiner* — Jacqueline F. Stephens
(74) *Attorney, Agent, or Firm* — Jordan and Hamburg LLP

(57) ABSTRACT

The present invention relates to a standing gather structure having skin-contact planar portions formed into a planer shape, which brings the entire skin-contact planar portions into tight contact with the user's skin, and provides the cushioning properties to soften a contact to the user's skin. The standing gathers BS each include a first wall portion standing upright from the proximal end, a second inner wall portion branching from the upper end portion of the first wall portion, a second outer wall portion branching outward from the upper end portion of the first wall portion and being positioned relatively outside the second inner wall portion, a skin-contact planar portion supported by the distal end portion of the second inner wall portion and the distal end portion of the second outer wall portion, a plurality of elastic members disposed on the skin-contact planar portion longitudinally along the napkin and a hollow portion defined by the skin-contact planar portion, the second inner wall portion and the second outer wall portion and positioned on the back surface side of the skin-contact planar portion.

12 Claims, 10 Drawing Sheets

ABSORPTIVE ARTICLE

BACKGROUND OF THE INVENTION

The present invention relates to an absorbent article such as sanitary napkins, ultra-thin sheet napkins for absorbing menstrual blood, vaginal discharge or the like and incontinence bladder control pads, and to an absorbent article including standing gathers which improve fitting to the user's body and has a cushioning properties.

In the related art, those having an absorbance member formed of cottony pulp or the like interposed between a liquid-impermeable back sheet such as polyethylene sheet or polyethylene sheet laminated non-woven fabric and a liquid-permeable top sheet such as a non-woven fabric or liquid-permeable plastic sheet are known as absorbent articles such as ultra-thin sheet napkins, sanitary napkins, incontinence bladder control pads.

The absorbent articles of this type have been improved repeatedly, and various countermeasures for preventing leakage of body fluid have been taken. As one of the countermeasures for preventing leakage of body fluid, a technology for forming standing gathers which serves as a barrier for side leakage along both sides on the surface side exists. As regards the standing gathers, solid gathers of T-shape in cross section having a planar skin-contact surface so as to improve the fitting to the user's skin and ensure prevention of leakage have been proposed.

For example, in Patent Document 1 shown below, as shown in FIG. 14, there is proposed an absorbent article N including a liquid-permeable surface layer 50, a liquid-impermeable back surface layer 51, a liquid-retainable absorbent layer 52 interposed between these layers, leakage preventing walls 54 provided so as to extend upright from the vicinities of left and right side edges of the absorbent layer 52, and a leakage preventing groove 55 having a predetermined shape formed on the surface layer side of the absorbent layer 52, in which the leakage preventing walls 54 each include a base wall portion 56, outwardly extending portion 57 and inwardly extending portion 58 extending respectively inwardly and outwardly of the absorbent article from the upper portion of the base wall portion, the outwardly extending portion 57 and the inwardly extending portion 58 each include an elastic member 59 disposed along the longitudinal direction thereof, and the outwardly extending portion 57 is positioned above the absorbent layer 52 and outwardly of the leakage preventing groove 55.

Patent Document 1: JP-A-2002-656

SUMMARY OF THE INVENTION

However, the invention disclosed in Patent Document 1 described above, in a state of a product in which an elastic force is introduced into the elastic member 59, the distal end of the inwardly extending portion 57 and the distal end of the outwardly extending portion 58 are lifted upward from the top of the base wall portion 56, and hence the cross-sectional view of the both extending portions 57, 58 are in the V-shape as shown in FIG. 15. Consequently, there arise problems such that it cannot be fitted to the user's skin, gaps are apt to be generated, and it gives a contact feeling to the wearer and hence the wearer may have uncomfortable feeling.

It is a main object of the present invention to provide a standing gather structure of a absorption article having a planer skin-contact surface, in which a skin-contact surface is entirely brought into fit to the user's skin to prevent easy formation of a gap, cushioning properties are provided to soften a contact to the user's skin, and the cushioning properties prevent generation of gaps around legs.

The present invention according to a first aspect thereof for solving the above-described problems, there is provided an absorption article including an absorbent member interposed between liquid-permeable top sheet and back sheet and standing gathers provided respectively on both side portions on the front surface side, wherein the standing gathers each include a first wall portion standing upright from the proximal end, a second inner wall portion branching from the upper end portion of the first wall portion, a second outer wall portion branching outward from the upper end portion of the first wall portion and being positioned relatively outside the second inner wall portion, a skin-contact planar portion supported by the distal end portion of the second inner wall portion and the distal end portion of the second outer wall portion, a plurality of elastic members disposed on the contact planar portion longitudinally along the absorption article, and a hollow portion defined by the contact planar portion, the second inner wall portion and the second outer wall portion and positioned on the back surface side of the contact planar portion.

In the standing gather structure according to the first aspect of the present invention, since the skin-contact planar portion is particularly adapted to be supported at two points of the second inner wall portion and the second outer wall portion, it is prevented to be V-shape in cross section by a resilient elastic force introduced thereto as in the case of the so-called T-shaped cross-sectional standing gather in the related art, and the entire contact planar portion comes into abutment uniformly with the skin, so that the structure in which the gap is hardly generated is achieved. Since the hollow portion exists on the back surface side of the contact planar portion, it comes into contact with the skin softly, and the cushioning properties are improved, so that the gap is hardly generated around the legs.

As a second aspect of the invention, there is provided the absorption article of the first aspect of the invention, in which the wall length of the second outer wall portions is longer than the wall length of the second inner wall portions, so that the level of the outer edges of the contact planar portions is higher than the level of the inner edges of the contact planar portions in the standing state.

According to the second aspect of the invention, since the flexibility on the side of the second outer wall portion is increased by setting the wall length of the second inner wall portion to be longer than the wall length of the second outer wall portion, the level of the outer edge of the contact planar portion is higher than the level of the inner edge of the contact planar portion in a state in which an elastic force of the elastic member is exerted. Therefore, the contact planar portions do not collapse outward in the worn state, and hence the contact surfaces can be brought into tight contact with the user's skin.

As a third aspect of the invention according to claim 3, there is provided the absorption article of the first and second aspects of the invention, in which the contact planar portion includes an inwardly extending portion projecting inwardly of the joint portion with respect to the second inner wall portion and an outwardly extending portion projecting outwardly of the joint portion with respect to the second outer wall portion, and the inwardly extending portion and the outwardly extending portion include elastic members respectively at the side edge positions thereof.

According to the third aspect of the invention, the extending portions are provided at the both side edge portions of the contact planar portions respectively, and the elastic members are arranged at side edges of the extending portions. Therefore, the side edge portions of the contact planar portions are easily lifted, and hence the contact planar portions assume an arcuate shape in cross-section as a whole, so that the degree of tight contact with the user's skin is increased and leakage is prevented further reliably.

As a fourth aspect of the invention, there is provided the absorption article described in any of the first to third aspects of the invention, in which second standing gathers are provided outside the standing gathers, so that upright standing and contact of the second standing gathers aid the outside portions of the contact planar portions of the standing gathers to stand upright.

In the fourth aspect of the invention, the second standing gathers are provided outside the standing gathers, and the standing action of the second standing gathers and the contact action of the standing gathers aid the outside portions of the contact planar portions of the standing gathers to stand upright. Therefore, the outside portions of the contact planar portions of the standing gathers are positively lifted with the aid of the second standing gathers to stand upright, so that the contact planar portions are prevented from collapsing outward, and side leakage is prevented by the double standing gathers further reliably.

As a fourth aspect of the invention, there is provided the absorption article described in any of the first to fourth aspects of the invention, in which part or the entire portion of the first wall portion and the second wall portion is provided with a water-impermeable film therein and the contact planar portions are not provided with the water-impermeable film therein.

According to the fifth aspect of the invention, part or the entire portion of the first wall portions and the second wall portions are provided with water-impermeable films therein and the contact planar portions are not provided with the water-impermeable film therein. Therefore, seepage from the sides of the absorbent member is prevented by the water-impermeable films disposed in the first wall portions, and seepage from the contact planar portions is prevented by the second outer wall portions. Since the water-impermeable film is not provided in the contact planar portions, uncomfortable contact to the user's skin is prevented. Preferably, the water-impermeable film is a film with good air permeability.

As a sixth aspect of the invention, there is provided the absorption article of the fifth aspect of the invention in which extending portions of the water-impermeable films cover the side edge portions of the absorbent member from the upper surface side.

According to the sixth aspect of the invention, the extending portions of the water-impermeable films cover the side edge portions of the absorbent member from the upper surface side, so that body fluid absorbed once by the absorbent member is prevented from coming out to the outside from the side edge portions.

As the seventh aspect of the invention, there is provided the absorption article of the fifth aspect of the invention in which the extending portions of the water-impermeable films wrap the side edge portions of the absorbent member and extend to the back side of the absorbent member, thereby covering the side edge portions of the absorbent member.

According to the seventh aspect of the invention, the extending portions of the water-impermeable films wrap the side edge portions of the absorbent member, and hence the body fluid absorbed once by the absorbent member is prevented from coming out from the side edge portions.

As described above, the present invention relates to the standing gather structure of the absorption article in which the skin-contact surfaces are formed into a planer shape so that the entire skin-contact surface is brought into tight contact with the user's skin, and hence gap is hardly generated. With the provision of a hollow portion on the back surface side of the contact planar portion, good cushioning properties are achieved, and it comes into contact with the skin softly, and with the increase of cushioning properties, the gap is hardly generated around the legs.

Embodiments of the present invention will be described in detail with reference to the drawings.

DETAILED DESCRIPTION OF THE INVENTION

Figure 1:
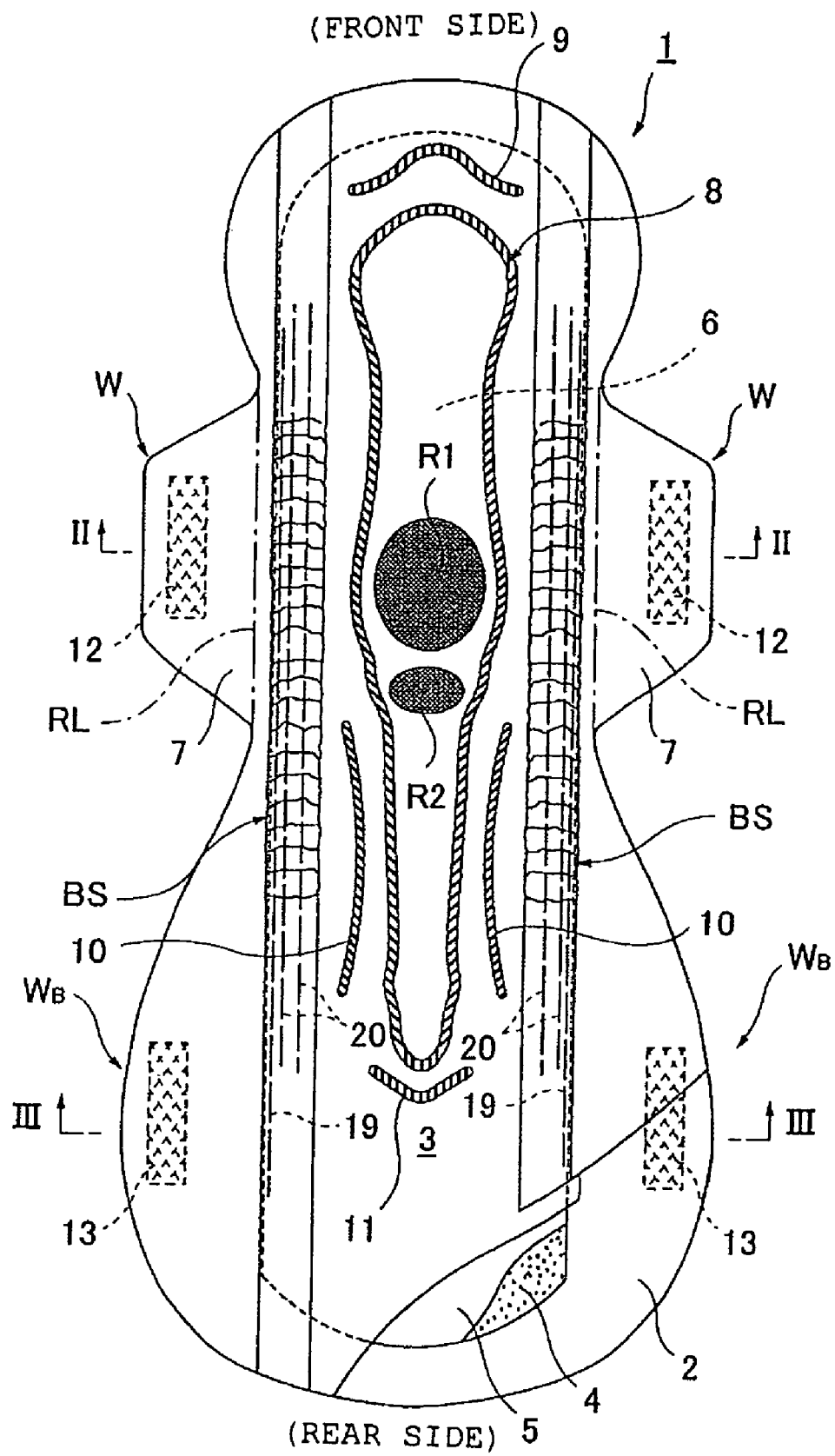
FIG. 1 is a deployed view of a sanitary napkin 1 according to the present invention.

The sanitary napkin 1 mainly includes a liquid-impermeable back sheet 2 formed of a polyethylene sheet or the like, a liquid-permeable top sheet 3 for allowing menstrual blood or vaginal discharge to rapidly pass through, absorbent members 4, 6 formed of cottony pulp, synthetic pulp or the like interposed between the both sheets 2, 3, a crape sheet 5 for surrounding the absorbent member 4 for maintaining the shape and improving the diffusing property of the absorbent member 4, and a pair of left and right standing gathers BS, BS provided so as to extend upright from substantially side edge portions of the absorbent member 4 and project on the surface side within a predetermined section in the fore-and-aft direction so as to include at least a body fluid discharging portion. The circumference of the absorbent member 4 is joined in such a manner that the upper and lower edge portions are joined by adhering the outer edge portions of the liquid-impermeable back sheet 2 and the liquid-permeable top sheet 3 with adhesive agent such as hot melt or adhesive means such as heat seal, and the both side edge portions are joined by adhering the liquid-impermeable back sheet 2 extending sideward from the absorbent member 4 and a side non-woven fabrics 7 which form the standing gathers BS by the adhesive agent such as hot melt or the adhesive means such as heat seal. Laminated sheet portions composed of the liquid-impermeable back sheet 2 and the side non-woven fabrics 7 are formed into sideward projecting wing flaps W, W and second wing flaps $W_B$, $W_B$ at positions on the side which corresponds to the user's hip.

The structure of the sanitary napkin 1 will be described further in detail below.

The liquid-impermeable back sheet 2 is formed of a sheet material having at least seepage control properties such as polyethylene. However, in recent years, there is a tendency that a material having moisture permeability is employed in terms of stuffiness. As the seepage controllable and moisture permeable sheet material, a microporous sheet obtained by forming a sheet by melting and mixing inorganic bulking agent in an olefin-based resin such as polyethylene or polypropylene, and then extending the same uniaxially or biaxially is preferably used. The liquid-impermeable back sheet 2 is formed with one of more ridges of adhesive agent layers (not shown) on a surface-not-to-be-used (outer surface), so that the sanitary napkin 1 can be fixed to an underwear when wearing it to the body. The liquid-impermeable back sheet 2 may be formed of "polylami" non-woven fabric formed by laminating a plastic film and a non-woven fabric.

Subsequently, as the liquid-permeable top sheet 3, a perforated or non-perforated non-woven fabric or porous plastic sheet are preferably used. Applicable material fibers which constitute the non-woven fabric include olefin-based, polyester-based and polyamide-based synthetic fibers such as polyethylene or polypropylene, recycled fibers such as rayon or cuprammonium, and natural fibers such as cotton, and non-woven fabrics obtained by suitable manufacturing methods such as span-lace method, span-bond method, thermal-bond method, melt-blown method, needle punch method, and so on. From among existing manufacturing methods, Span-lace Method is superior in having flexibility and draping characteristics, and Thermal Bond Method is superior in bulkiness and softness. When a number of through holes are formed on the liquid-permeable top sheet 3, menstrual blood, virginal discharge, or the like (hereinafter, referred representatively as body fluid) is rapidly absorbed, and hence a property superior in dryness is achieved.

The absorbent member 4 must simply be able to absorb and retain body fluid, and the one obtained normally by mixing water-absorbing polymer powder in a flap pulp is preferably used in terms of absorbing property and price. The absorbent member 4 is preferably wrapped by the crape sheet 5, for example, for keeping the shape.

On the surface-to-be-used of the absorbent member 4, a center-high-portion 6 of the absorbent member which has a height from the surface-to-be-used is formed at the widthwise center in an area elongated longitudinally of the napkin and defined by the emboss 8 which is formed in the circumferential direction. The thickness of the center-high-portion 6 is from 3 to 20 mm, preferably, from 5 to 15 mm since excessive thickness increases the rigidity of the absorbent member 4 and hence deteriorates the fitting to the body. On the surface-to-be-used is formed with embosses 9, 10, 11 in addition to the emboss 8. The respective embosses 8 to 11 will be described later further in detail.

Figure 2:
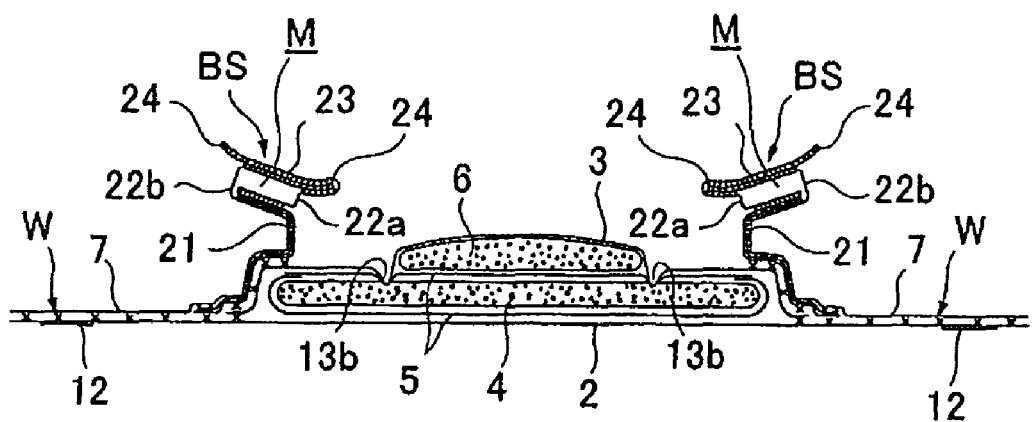
FIG. 2 is a lateral cross section thereof (a cross-sectional view taken along the line II-II in FIG. 1).
Figure 3:
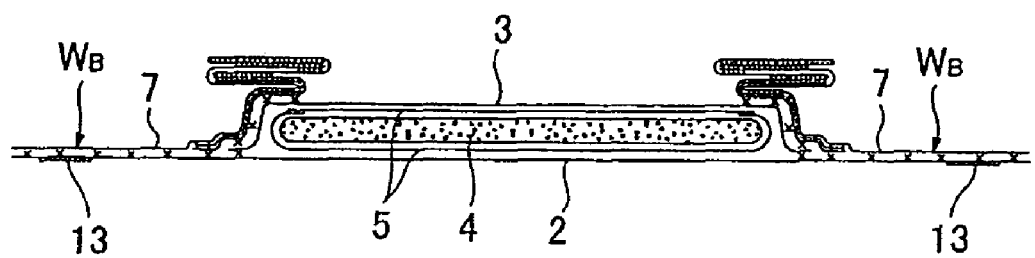
FIG. 3 is a lateral cross section thereof (a cross-sectional view taken along the line III-III in FIG. 1).

On the other hand, the width of the liquid-permeable top sheet 3 is slightly larger than the width of the absorbent member 4 as shown in the lateral cross-sectional views in FIG. 2 and FIG. 3 for example, and simply covers the absorbent member 4. The standing gathers BS are formed of the side non-woven fabrics 7 which are different from the liquid-permeable top sheet 3, more specifically, of a non-woven material applied with water-repellant finishing or hydrophilic finishing as needed according to the object, such as, to prevent menstrual blood, vaginal discharge from permeating or to enhance its soft-touch feeling. The side non-woven fabrics 7 as described above may be of the one formed by a suitable manufacturing method with a material such as natural fibers, synthetic fibers, or recycled fibers. However, a non-woven fabric having a low grammage and ensuring air flow is preferable for eliminating stiffness and preventing stuffiness. More specifically, a non-woven fabric manufactured to have a grammage of 18 to 23 $g/m^2$ is preferable, and a water-repellant finished non-woven fabric coated with silicon-based, paraffin-based, or alkyl-chromic-chloride-based water-repellant agent for positively preventing body fluid to pass through is preferably used.

Figure 13:
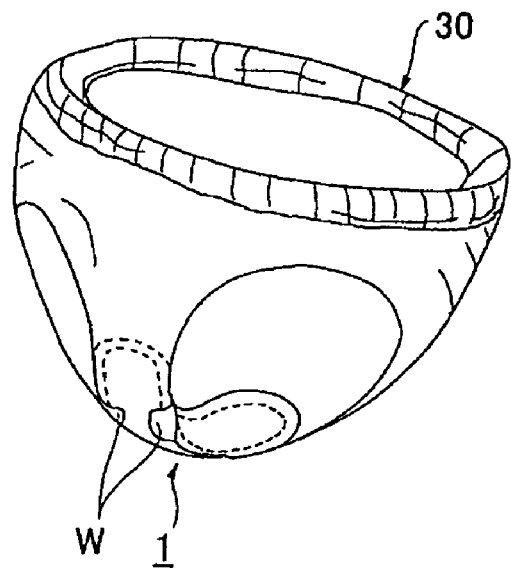
FIG. 13 is a perspective view showing a state of attachment of the napkin.
Figure 14:
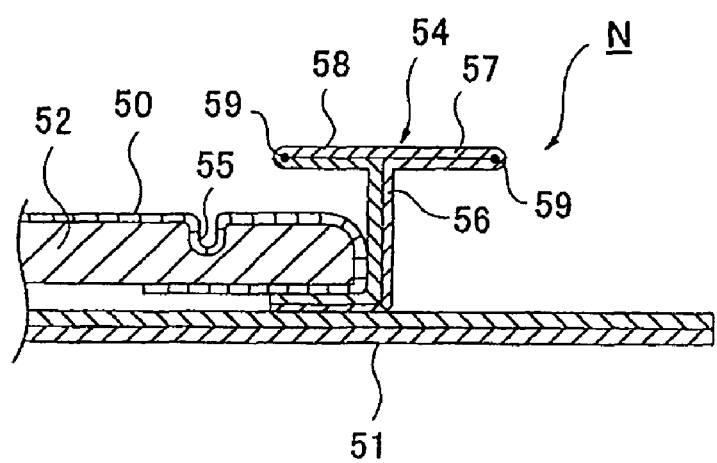
FIG. 14 is a cross-sectional view showing a T-shaped standing gather in the related art.
Figure 15:
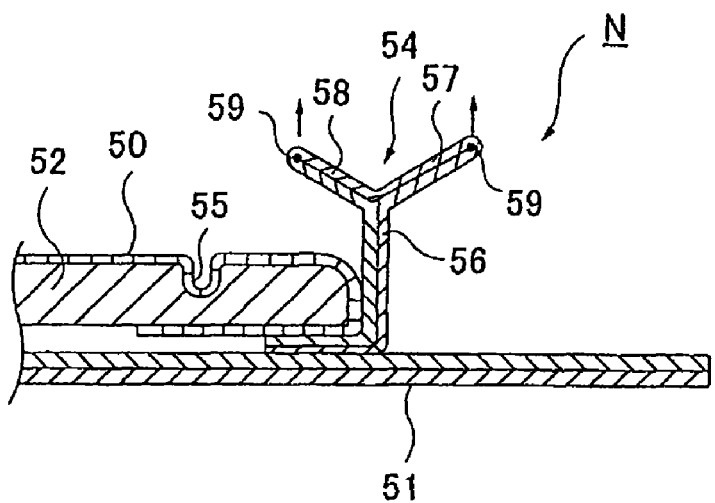
FIG. 15 is a cross-sectional view showing an actual standing state thereof.

As shown in FIG. 2 and FIG. 3, the side non-woven fabrics 7 are adhered at portions outside from the widthwise mid section over an area from positions inside the absorbent member 4 slightly beyond the side edges of the absorbent member to the outer edge of the liquid-impermeable back sheet 2 with the adhesive agent such as hot melt, and the laminated sheet portions including the side non-woven fabrics 7 and the liquid-impermeable back sheet 2 constitute the pair of left and right wing flaps W, W on the sides of the absorbent member, which substantially corresponds to the body fluid discharging portion, and constitute the second wing flaps $W_B$, $W_B$ at positions on the side which corresponds to the user's hip. The outer surfaces of the wing flaps W, W and the second wing flaps $W_B$, $W_B$ are formed with adhesive layers 12 . . . , 13 . . . , respectively, as shown in FIG. 13, so that the napkin is attached to a panty 30 by folding the wing flaps W, W back to the opposite side along a folding line RL, wrapping around a crotch portion of the panty, and being secured thereto.

On the other hand, the standing gathers BS formed by the side non-woven fabrics 7 are standing gathers each including a first wall portion 21 standing upright from the proximal end, a second inner wall portion 22a branching from the upper end portion of the first wall portion 21, a second outer wall portion 22b branching outward from the upper end portion of the first wall portion 21 and being positioned relatively outside the second inner wall portion 22a, a skin-contact planar portion 23 supported by the distal end portion of the second inner wall portion 22a and the distal end portion of the second outer wall portion 22b, a plurality of elastic members 24, 24 . . . disposed on the skin-contact planar portion 23 longitudinally along the sanitary napkin 1, and a hollow portion M defined by the skin-contact planar portion 23, the second inner wall portion 22a and the second outer wall portion 22b and positioned on the back surface side of the skin-contact planar portion 23 as shown in FIG. 2. The standing gathers BS is adhered to the absorbent member 4 side in a folded and laminated state at the front and rear end portions of the sanitary napkin 1 as shown in FIG. 3.

Referring now to FIG. 4, the structure of the standing gathers BS will be described further in detail. X-signs in the drawing represent adhered portion. The inner side means the center side of the napkin 1 and the outer side means the outside of the napkin 1.

As shown in FIG. 4, the standing gather BS is composed of folded two layers of side non-woven fabric 7. As shown in FIG. 4(A), the standing gather forming portion of the side non-woven fabric 7 is folded into four layers of a first laminated portion $S_1$, a second laminated portion $S_2$, a third laminated portion $S_3$ and a fourth laminated portion $S_4$. The inner sides of the third laminated portion $S_3$ and the fourth laminated portion $S_4$ are slightly protruded. A water-impermeable film 25 is provided in the interior of the seat at the first laminated portion $S_1$ and the second laminated portion $S_2$, and a plurality of elastic members 24, 24 . . . , more specifically, five elastic members 24, 24 . . . in total are disposed on the fourth laminated portion $S_4$ at both end portions and the mid sections along the longitudinal direction of the napkin 1.

As regards adhesion of the two layers of the side non-woven fabrics 7, at the portion of the third laminated portion $S_3$, only part A on the right end side is adhered with adhesive agent and other portion B is not adhered. As regards joining of the boundaries of the first laminated portion $S_1$ to the fourth laminated portion $S_4$, the boundary between the first laminated portion $S_1$ and the second laminated portion $S_2$ is not adhered, the boundary between the second laminated portion $S_2$ and the third laminated portion $S_3$ is adhered except for a part at the inner end, and the boundary between the third laminated portion $S_3$ and the fourth laminated portion $S_4$ is adhered except for a part on the outer side.

Figure 4A:
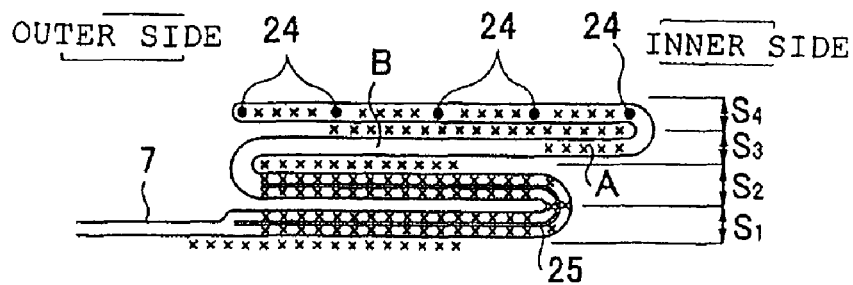
FIG. 4 is pattern diagrams (A) to (D) showing examples of structures of standing gather BS formation.
Figure 4B:
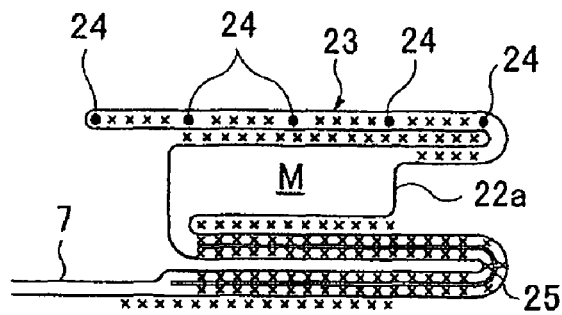
Figure 4C:
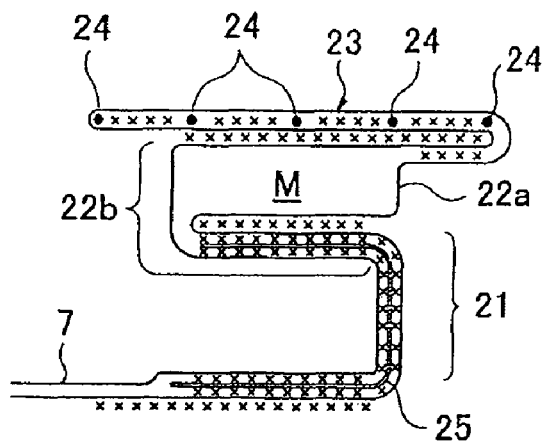

Therefore, when an elastic force is introduced into the elastic members 24, 24 . . . , as shown in FIG. 4(B), the upper sheet portions of the fourth laminated portion $S_4$ and the third laminated portion $S_3$ are integrally lifted, and as shown in FIG. 4(C), the inwardly folded portion of the first laminated portion $S_1$ and the second laminated portion $S_2$ stands upright.

In the state in FIG. 4(C), the lower layer sheet of the third laminated portion $S_3$ and the upper sheet portions of the fourth laminated portion $S_4$ and the third laminated portion $S_3$ which are separated and lifted upward from the second laminated portion $S_2$ constitute the contact planar portion 23, the inner non-adhered sheet portion (single layer) of the third laminated portion $S_3$ constitutes the second inner wall portion 22a, the outer upper non-adhered sheet portion (single layer) of the third laminated portion $S_3$ and the outer portion of the second laminated portion $S_2$ constitute the second outer wall portion 22b, and the standing portion of the inner portion of the first laminated portion $S_1$ and the inner portion of the second laminated portion $S_2$ constitute the first wall portion 21.

Figure 4D:
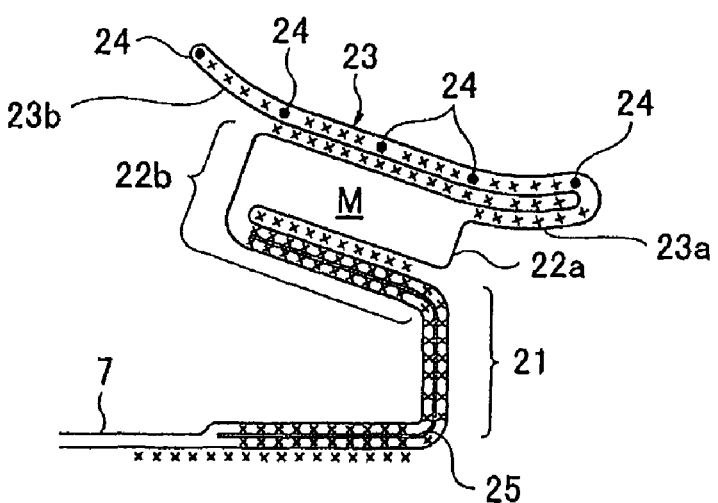

Furthermore, since the wall length of the second outer wall portion 22b is longer than the wall length of the second inner wall portion 22a, the flexibility is higher on the side of the second outer wall portion 22b, and hence the standing extent caused by the elastic members 24, 24 . . . is increased. Therefore, as shown in FIG. 4(D), in the standing state, the level of the outer edge of the contact planar portion 23 is higher than the level of the inner edge of the contact planar portion.

Figure 5:
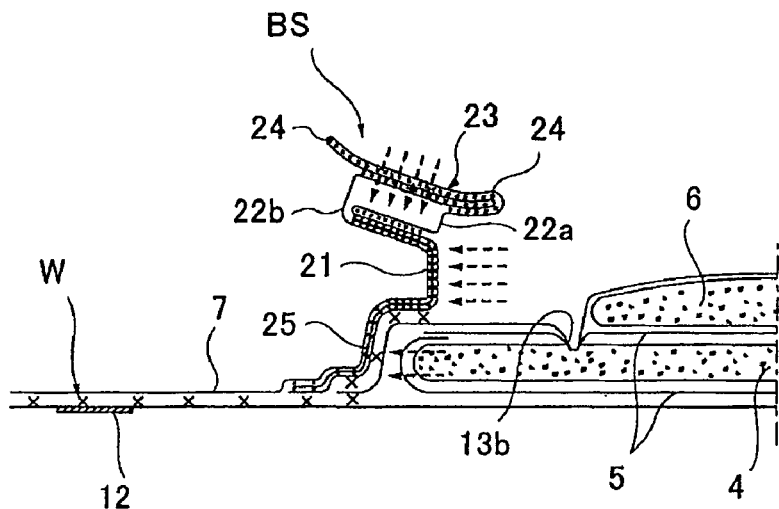
FIG. 5 is a lateral cross section of the standing gather BS.
Figure 6:
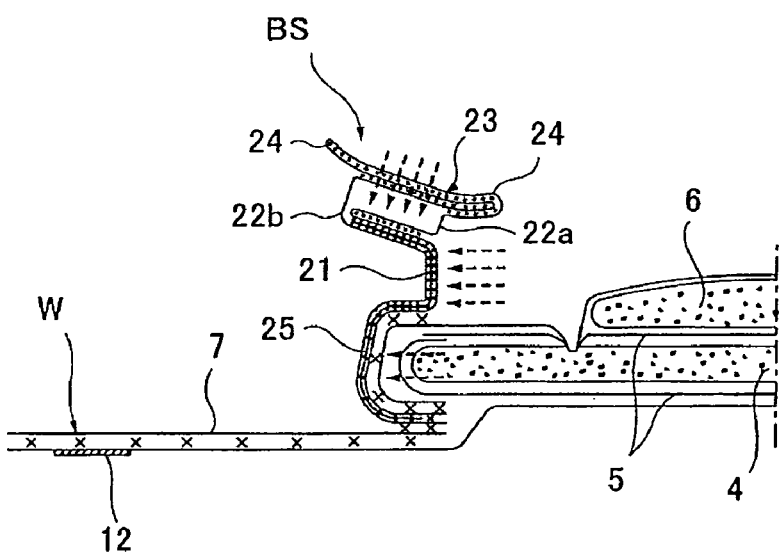
FIG. 6 is a lateral cross section of the standing gather BS according to a modification.

As is understood from the same drawing 4(D), the contact planar portion 23 includes an inwardly extending portion 23a projecting inwardly from the joint portion with respect to the second inner wall portion 22a and an outwardly extending portion 23b projecting outward from the joint portion with respect to the second outer wall portion 22b, and the both side edge portions are lifted upward by the elastic force of the elastic members 24, 24 arranged at both end portions of the contact planar portion 23, so that the contact planar portion 23 assumes a substantially arcuate shape in cross section. Seepage of body fluid is prevented by the water-impermeable film 25 which is provided in the first wall portion 21 and a part (bottom portion) of the second outer wall portion 22b. More specifically, as shown in FIG. 5, in a mode in which the extending portion of the water-impermeable film 25 covers the side edge portion of the absorbent member 4 from the upper surface side, body fluid passed through the contact planar portion 23 is blocked by the water-impermeable film 25, and seepage of body fluid running on the upper surface of the top sheet 3 and body fluid absorbed by the absorbent member 4 from the side edge portion is blocked by the water-impermeable film 25 provided in the first wall portion 21. As shown in FIG. 6, the water-impermeable film 25 may be arranged so as to extend to the back side of the absorbent member 4 while wrapping the side edge portion of the absorbent member 4 and cover the side edge portion of the absorbent member. The effect achieved in this case is the same.

Figure 7:
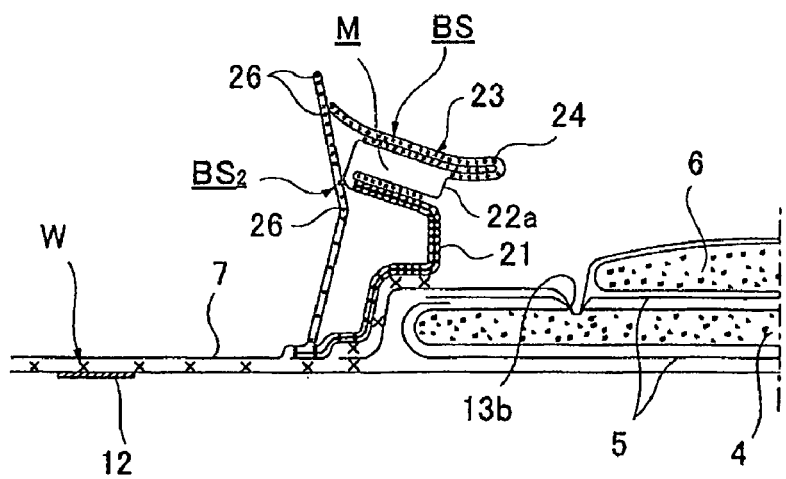
FIG. 7 is a lateral cross section of the standing gather BS according to another modification.

As shown in FIG. 7, a second standing gather $BS_2$ may be provided on the outside of the standing gathers BS. The second standing gather $BS_2$ is composed of a double sheet portion extending from the side non-woven fabrics 7, and the suitable number of elastic members 26, 26 . . . disposed therein, so that it is stood up by the elastic force thereof. with the arrangement of the second standing gather $BS_2$ in the proximity of the standing gathers BS, it comes into contact with the outside portion of the contact planar portion 23 when stood up and aids the standing up movement thereof.

Figure 8:
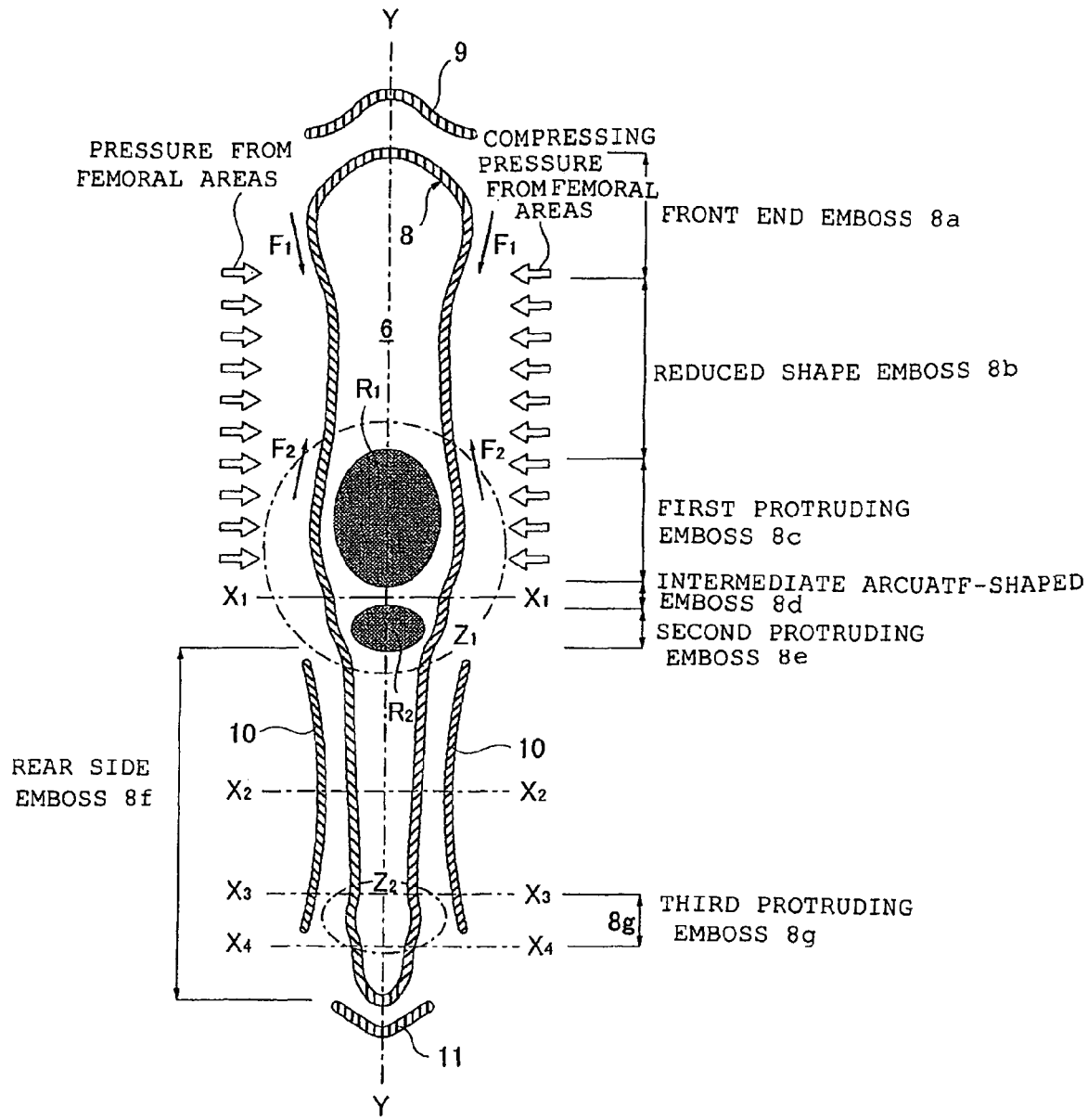
FIG. 8 is an explanatory drawing showing embosses 8 to 11.

Specifically, as shown in FIG. 8, the sanitary napkin 1 includes the center-high-portion 6 of the absorbent member which has a height on the surface-to-be-used at the widthwise center, and the emboss 8 elongated longitudinally of the napkin 1 is formed so as to surround the center-high-portion 6. The emboss 8 includes a front end emboss 8a, a reduced shape emboss 8b, a first protruding emboss 8c, an intermediate arcuate-shaped emboss 8d, a second protruding emboss 8e and a rear side emboss 8f in sequence from the front. The respective embosses are formed continuously without disconnection, and are closed as a whole in the circumferential direction.

The front end emboss 8a is an emboss which is formed into substantially a semi-circular shape, and connects a pair of left and right emboss extending along the substantially longitudinal direction formed respectively on both sides of the center-high-portion 6 at the front end portion of the napkin with a curved line.

The reduced shape emboss 8b is a pair of left and right emboss lines formed so as to extend longitudinally of the napkin 1 on both sides of the center-high-portion 6 so as to continue from the front end emboss 8a, and is positioned substantially at the front side of the femoral regions. As shown in the drawing, the emboss lines on both sides are each composed of a curved line having a center of curvature outside the napkin 1, thereby forming a reduced area in emboss-to-emboss distance.

The first protruding emboss 8c includes a pair of left and right emboss lines formed so as to extend substantially longitudinally of the napkin 1 on both sides of the center-high-portion 6 so as to continue from the reduced shape emboss 8b, and is positioned substantially at the rear side of the femoral regions. The emboss lines on both sides are each composed of a curved line having a center of curvature on the center side of the napkin 1, thereby forming an enlarged area in emboss-to-emboss distance.

Figure 9A:
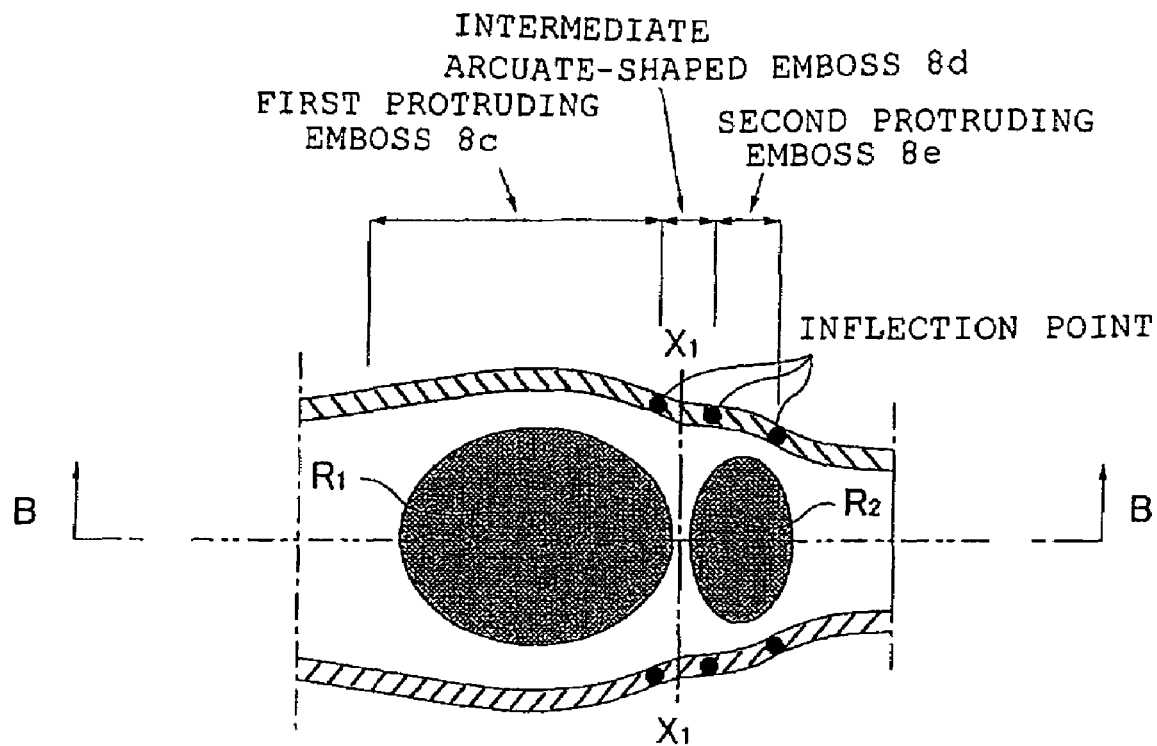
FIG. 9 illustrates (A) an enlarged principal portion thereof, and (B) a cross-sectional view taken along the line B-B.

The intermediate arcuate-shaped emboss 8d includes a pair of left and right emboss lines formed so as to extend substantially longitudinally of the napkin 1 on both sides of the center-high-portion 6 so as to continue from the first protruding emboss 8c. More specifically, as shown in FIG. 9, the both emboss lines are each composed of a curved line having a center of curvature outside the napkin 1 so as to extend over a very short section with the boundary at an infection point where the position of the center of curvature is inverted.

The second protruding emboss 8e includes a pair of left and right emboss lines formed so as to extend substantially longitudinally of the napkin 1 on both sides of the center-high-portion 6 so as to continue from the intermediate arcuate-shaped emboss 8d. More specifically, as shown in FIG. 9, the both emboss lines are each composed of a curved line having a center of curvature on the center side of the napkin 1 with the boundary at an infection point where the position of the center of curvature is inverted. The second protruding emboss 8e is formed over a relatively shorter section than the first protruding emboss 8c.

The rear side emboss 8f includes a pair of left and right emboss lines formed so as to extend substantially longitudinally of the napkin 1 on both sides of the center-high-portion 6 so as to continue from the second protruding emboss 8e. In the example shown in the drawing, it extends to the rear side so as to reduce the emboss-to-emboss distance gradually little by little, and on the rear side, the both embosses are connected by an arcuate-shaped curved emboss. Formed at the mid section on the rear side from the center of the rear side emboss 8f is a third protruding emboss 8g formed so as to define an area enlarged in emboss-to-emboss distance composed of curved lines having the center of curvatures on the center side of the napkin 1.

Formed outside the rear side emboss 8f are second rear side embosses 10, 10 extending longitudinally of the napkin 1 at a distance form the rear side embosses 8f. In the example shown in the drawing, the second rear side embosses 10 are each formed into an arcuate line having a center of curvature outside the napkin 1.

Formed on the front side of the front end emboss 8a is a front end independent emboss 9 formed into a substantially umbrella shape at a distance, and formed on the rear side of the rear side emboss 8f is a rear end independent emboss 11 formed into a substantially inverted umbrella shape at a distance.

With the respective embosses 8 to 11 formed as described above, the following effects are achieved.

First of all, in an area in which the first protruding emboss 8c, the intermediate arcuate-shaped emboss 8d and the second protruding emboss 8e are formed, the areas in which the protruding embosses 8c, 8e are formed are areas which can hardly be bent along a flexible line (folding line) in the direction of the width of the napkin due to the outwardly protruding emboss lines as shown in FIG. 9 in detail. However, the intermediate arcuate-shaped emboss 8d which is interposed between these protruding embosses 8c, 8e is an area in which the emboss curves are inverted, a force to restrain the distortion of the respective protruding embosses 8c, 8e is released, and hence can relatively be bent easily along a flexible line $X_1$-$X_1$ in the direction of the width of the napkin.

On the other hand, assuming that the napkin 1 is attached to the panty 30 as shown in FIG. 13, the areas of the reduced shape emboss 8b and the first protruding emboss 8c receive an inward compression force from the femoral regions, and the compression force compresses the absorbent member 4 in the widthwise direction and, simultaneously, the force is transmitted through the embosses 8 formed longitudinally of the napkin, so that inwardly directed action forces F1, F2 act on the front side and the rear side. When the crotch portion of the panty 30 is further pulled upward toward the body, the napkin 1 receives a pressing force which presses the napkin against a portion between the legs along the longitudinal centerline Y-Y.

With the action force as described above, a first raised portion $R_1$ is formed in $Z_1$ area at a portion of the first protruding emboss 8c which corresponds to blood discharge opening, and the raised portion $R_1$ comes into tight contact with the portion near the blood discharge opening, so that menstrual blood or the like is absorbed. A second raised portion $R_2$ is formed at a portion of the second protruding emboss 8e which corresponds to the perineal region extending from the vaginal opening rearward to a portion near the anal via the intermediate arcuate-shaped emboss 8d formed with the $X_1$-$X_1$ flexible axis and the second raised portion $R_2$ comes into tight contact with the perineal region, so that menstrual blood or the like which is failed to be absorbed by the portion near the blood discharge opening is reliably absorbed, and leakage of body fluid running rearward can reliably be prevented.

Figure 9B:
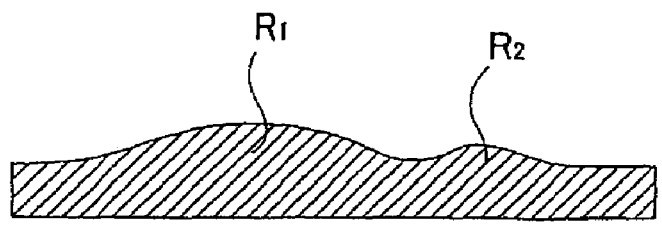

In other words, as shown in FIG. 9(B), the area of the intermediate arcuate-shaped emboss 8d is free from the distortion in the raising direction, and the raised portions $R_1$, $R_2$ are formed in the area of the first protruding emboss 8c and the area of the second protruding emboss 8e positioned in front and back of the $X_1$-$X_1$ flexible axis as if two mountains are continued because of the existence of the $X_1$-$X_1$ flexible axis. Therefore, the first raised portion $R_1$ comes into tight contact with the portion near the blood discharging opening and the second raised portion $R_2$ comes into tight contact with the portion near the perineal region, so that leakage of running menstrual blood or the like can reliably prevented. The second raised portion $R_2$ is formed to be smaller than the first raised portion $R_1$ in proportion to the scale of formation of the second protruding emboss 8e.

On the other hand, in the area of the rear side emboss 8f, the second rear side embosses 10 are formed respectively on both sides of the center-high-portion 6 longitudinally of the napkin 1 in addition to the rear side emboss 8f. Since these four ridges of embosses form the flexible axes respectively, the flexibility in the direction along the $X_2$-$X_2$ increase, and hence the fitting with respect to the valley portion of the hip is improved.

Furthermore, the third protruding emboss 8g formed at the rear side from the center of the rear side emboss 8f is adapted to be bent easily at the respective positions of transverse lines $X_3$-$X_3$, $X_4$-$X_4$ which correspond to the positions of the inflection points, and distortion in the direction of the vertical line Y-Y is disconnected at the positions of the respective inflection points, so that the area $Z_2$ is raised and fitted to the valley of the hip.

On the other hand, the aforementioned umbrella-shaped front end independent emboss 9 formed at the front most end of the napkin 1 serves as a flexible axis and makes the front end portion of the napkin 1 be bent easily, and the aforementioned inverted umbrella-shaped rear end independent emboss 11 formed on the rear side serves as a flexible axis and makes the left and right second wing flaps $W_B$, $W_B$ be bent easily.

Figure 10:
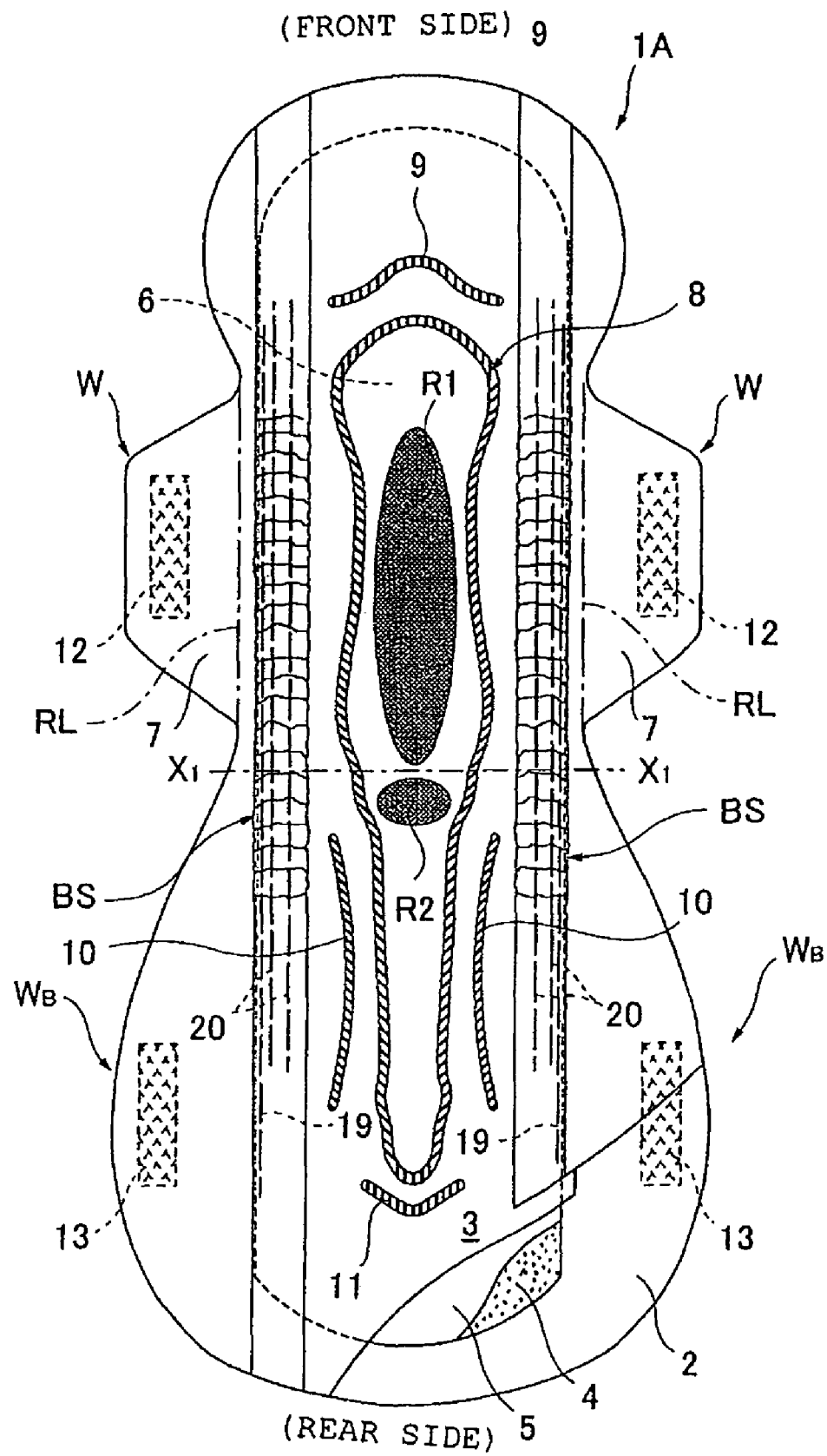
FIG. 10 is a deployed view of the sanitary napkin 1 in which the positions of the embosses 8 to 11 are shifted downward.

The position of the blood discharging opening generally corresponds fixedly to the position of the wing flaps W, W on the napkin 1. However, it is also possible to form the respective embosses 8 to 11 at positions shifted relatively downward so that the area of the reduced shape emboss 8b of the emboss 8 comes to a position corresponding to the wing flaps W, W, for example, as shown in FIG. 10.

Figure 11A:
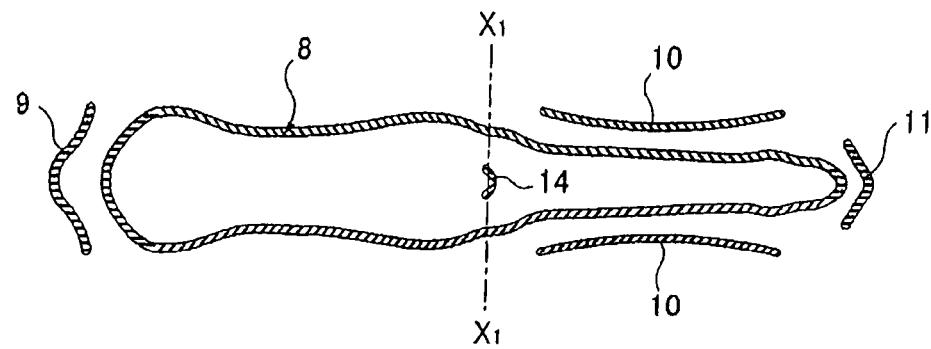
FIG. 11(A) to (C) illustrate modifications of the emboss, respectively.
Figure 11B:
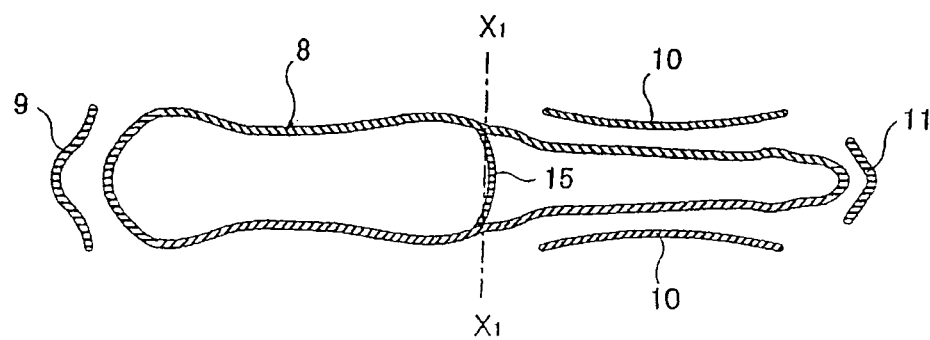

Other embodiments of the invention include:

(1) In order to make the napkin 1 be bent easily at the position of the flexible axis $X_1$-$X_1$ formed between the first protruding emboss 8c area and the second protruding emboss 8e area, auxiliary embosses extending substantially along the widthwise direction of the napkin 1 may be provided. FIG. 11(A) illustrates an example in which an arcuate emboss 14 oriented in the widthwise direction is formed at the widthwise center as the auxiliary emboss. FIG. 11(B) illustrates an example in which an arcuate emboss 15 is formed in the widthwise direction so as to connect the embosses on the both sides.

Figure 11C:
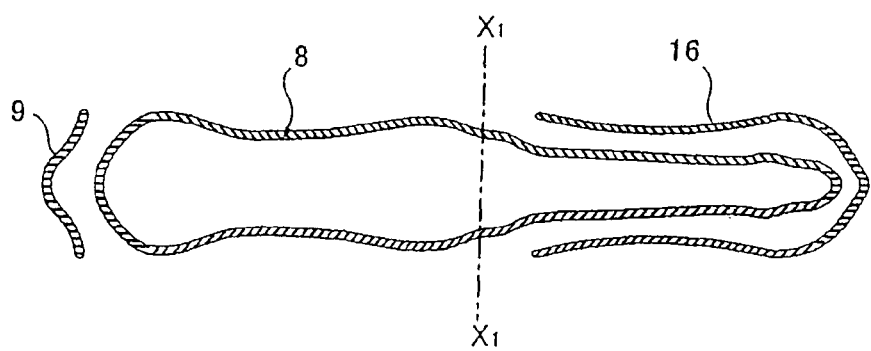

(2) In the embodiments shown above, the second rear side embosses 10, 10 are formed independently. However, as shown in FIG. 11(C), the second rear side embosses 10, 10 and the rear end independent emboss 11 are connected so that a continuous emboss 16 of a substantially U-shape may be formed.

Figure 12:
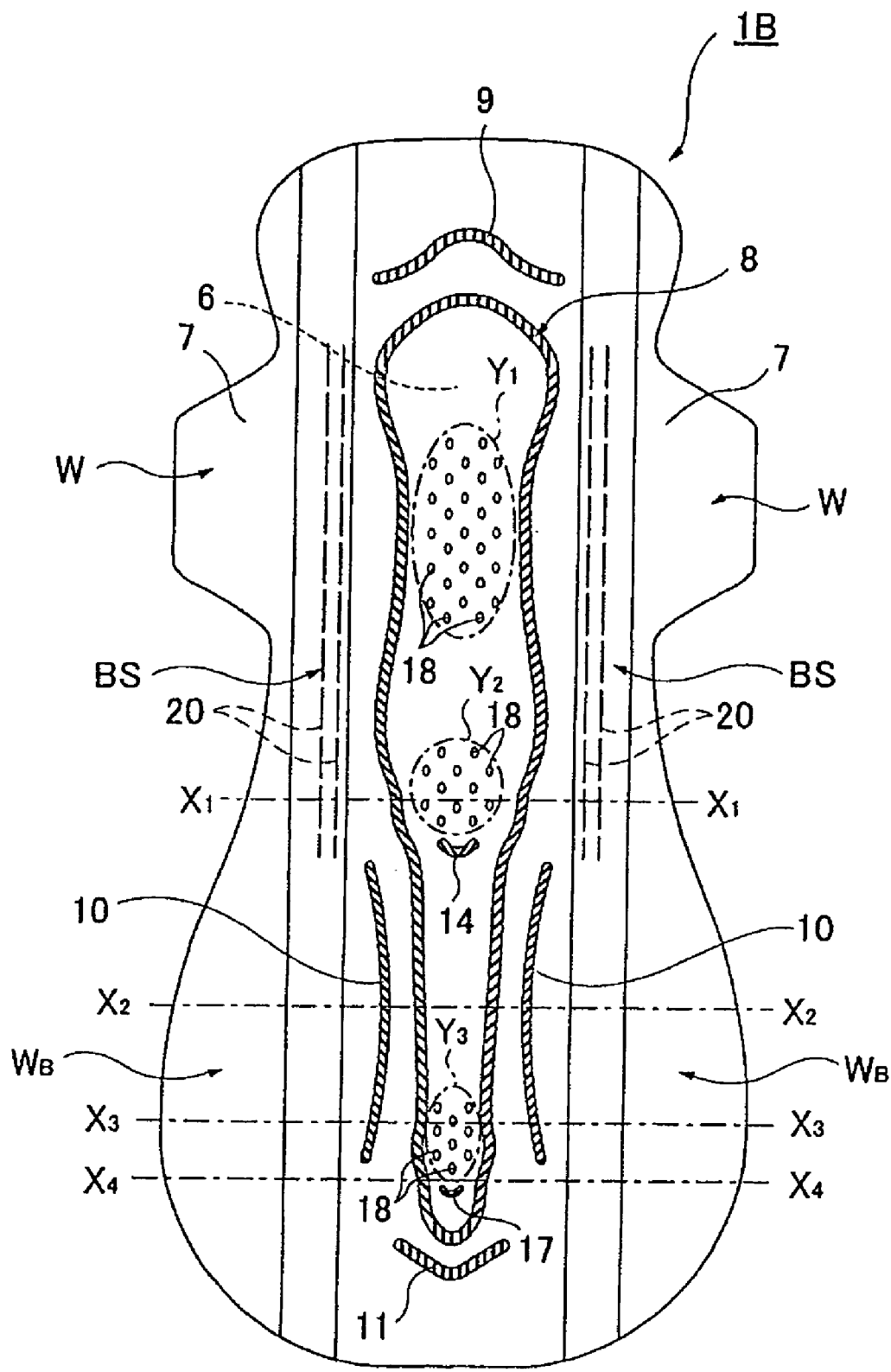
FIG. 12 is a deployed view showing another mode of formation of the emboss.

(3) Furthermore, as shown in FIG. 12, it is preferable to form a number of dot embosses 18, 18... of in the form of fine depressions on the surface of the center-high-portion 6 in the area $Y_1$ including the blood discharging portion, the area $Y_2$ including the portion corresponding to the perineal region and the area $Y_3$ including the third protruding emboss 8g, so that the property of absorbing menstrual blood or the like is improved. In the example in the same drawing, arcuate-shaped embosses 14, 17 oriented respectively in the widthwise direction are formed at the widthwise center at the position adjacent to the flexible axis $X_1$-$X_1$ and the portion of the third protruding emboss 8g.

(4) In the embodiment shown above, the emboss 8 is formed by connecting the pair of left and right emboss lines at the front end portion and the rear end portion of the napkin, and is formed into a closed shape as a whole. However, a form in which the pair of left and right emboss lines are not connected at the front end portion and/or the rear end portion is also applicable.

The invention claimed is:

1. An absorption article comprising: an absorbent member interposed between liquid-permeable top sheet and back sheet and standing gathers provided respectively on both side portions on the front surface side,
   wherein the standing gathers each include a first wall portion standing upright from the proximal end, a second inner wall portion branching from the upper end portion of the first wall portion, a second outer wall portion branching outward from the upper end portion of the first wall portion and being positioned relatively outside the second inner wall portion, a skin-contact planar portion supported by the distal end portion of the second inner wall portion and the distal end portion of the second outer wall portion, a plurality of elastic members disposed on the contact planar portion longitudinally along the absorption article, and a hollow portion defined by the contact planar portion, the second inner wall portion and the second outer wall portion and positioned on the back surface side of the contact planar portion.

2. The absorption article according to claim 1, wherein the wall length of the second outer wall portions is longer than the wall length of the second inner wall portions, so that the level of the outer edges of the contact planar portions is higher than the level of the inner edges of the contact planar portions in a standing state.

3. The absorption article according to claim 1 or 2, wherein second standing gathers are provided outside the standing gathers, so that upright standing and contact of the second standing gathers aid the outside portions of the contact planar portions of the standing gathers to stand upright.

4. The absorption article according to claim 1 or 2, wherein part or the entire portion of the first wall portion and the second wall portion is provided with a water-impermeable film therein and the contact planar portions are not provided with the water-impermeable film therein.

5. The absorption article according to claim 4, wherein extending portions of the water-impermeable films cover the side edge portions of the absorbent member from the upper surface side.

6. The absorption article according to claim 4, wherein the extending portions of the water-impermeable films wrap the side edge portions of the absorbent member and extend to the back side of the absorbent member, thereby covering the side edge portions of the absorbent member.

7. The absorption article according to claim 1 or 2, wherein the contact planar portion includes an inwardly extending portion projecting inwardly of the joint portion with respect to the second inner wall portion and an outwardly extending portion projecting outwardly of the joint portion with respect to the second outer wall portion, and the inwardly extending portion and the outwardly extending portion include elastic members respectively at the side edge positions thereof.

8. The absorption article according to claim 1, wherein the first wall portion, the second inner wall portion branching, the second outer wall portion, and the skin-contact planar portion each are formed from non-woven fabric distinct from and excluding the top sheet and back sheet.

9. The absorption article according to claim 1, wherein the hollow portion is collapsible to bring distal and proximal walls of the hollow portion into contact and reduce the height of the standing gather.

10. An absorption article comprising:
   a liquid-permeable top sheet;
   a back sheet;
   an absorbent member interposed between the liquid-permeable top sheet and the back sheet; and
   standing gathers provided respectively at first and second side portions on a front surface of the article, and being formed by two continuous layers of fabric that are adhered to one another except for a first length, the standing gathers having a first fold in which one layer of the two layers is folded onto and adhered to itself and a second fold in which the other layer of the two layers is folded onto and adhered to itself;
   wherein the standing gathers each include a first wall portion standing upright from the proximal end, a second inner wall portion branching from the upper end portion of the first wall portion, a second outer wall portion branching outward from the upper end portion of the first wall portion and being positioned relatively outside the second inner wall portion, a skin-contact planar portion supported by the distal end portion of the second inner wall portion and the distal end portion of the second outer wall portion, a plurality of elastic members disposed on the contact planar portion longitudinally along the absorption article, and a hollow portion defined by the contact planar portion, the second inner wall portion and the second outer wall portion and positioned on the back surface side of the contact planar portion.

11. An absorption article comprising:
   a liquid-permeable top sheet;
   a back sheet;
   an absorbent member interposed between the liquid-permeable top sheet and the back sheet; and
   standing gathers provided respectively at first and second side portions on a front surface of the article, and being formed by two continuous layers of material that are folded, said two continuous layers being adhered to one another except for a first length;
   wherein the standing gathers each include:
      a first portion standing upright from a proximal end,
      a second portion continuous with and distal to the first portion, the second portion being formed at a first fold of the two continuous layers,
      a skin-contact planar portion distal to a distal second fold of the two continuous layers,
      a plurality of elastic members disposed on the contact planar portion longitudinally along the absorption article, and a hollow portion having first and second walls defined by said two continuous layers at said first length, wherein the first wall of the hollow portion is adjacent to a back surface side of the contact planar portion.

12. The absorption article according to claim 11, wherein the standing gathers have a plurality of folds, a first fold among the plurality of folds allowing a first wall of the hollow portion to contact and be adhered to a first wall of the contact planar portion.

* * * * *